United States Patent
Hancock et al.

(10) Patent No.: US 11,172,985 B2
(45) Date of Patent: Nov. 16, 2021

(54) ELECTROSURGICAL SNARE

(71) Applicant: CREO MEDICAL LIMITED, Chepstow (GB)

(72) Inventors: Christopher Paul Hancock, Bath (GB); Malcolm White, Chepstow (GB); Steven Morris, Chepstow (GB); Craig Gulliford, Chepstow (GB); Sandra May Bernadette Swain, Chepstow (GB); Mohammed Sabih Chaudhry, Chepstow (GB); Brian Saunders, Rickmansworth (GB)

(73) Assignee: CREO MEDICAL LIMITED, Chepstow (GB)

( * ) Notice: Subject to any disclaimer, the term of this patent is extended or adjusted under 35 U.S.C. 154(b) by 545 days.

(21) Appl. No.: 15/745,356

(22) PCT Filed: Sep. 6, 2016

(86) PCT No.: PCT/EP2016/070990
§ 371 (c)(1),
(2) Date: Jan. 16, 2018

(87) PCT Pub. No.: WO2017/042169
PCT Pub. Date: Mar. 16, 2017

(65) Prior Publication Data
US 2018/0206916 A1    Jul. 26, 2018

(30) Foreign Application Priority Data
Sep. 7, 2015    (GB) .................................... 1515828

(51) Int. Cl.
*A61B 18/18*    (2006.01)
*A61B 17/3205*    (2006.01)
(Continued)

(52) U.S. Cl.
CPC .... *A61B 18/1815* (2013.01); *A61B 17/32056* (2013.01); *A61B 17/221* (2013.01);
(Continued)

(58) Field of Classification Search
CPC ............ A61B 17/221; A61B 17/32056; A61B 18/1815; A61B 2017/2212;
(Continued)

(56) References Cited

U.S. PATENT DOCUMENTS 5,158,561 A  * 10/1992  Rydell .................... A61B 18/14
                                                        606/110
5,201,741 A  *  4/1993  Dulebohn ........ A61B 17/32056
                                                        606/113
(Continued)

FOREIGN PATENT DOCUMENTS

EP      0393279 A2    10/1990
GB      2521611 A      7/2015
(Continued)

OTHER PUBLICATIONS

British Search Report of related British Patent Application No. GB1515828.0 dated Feb. 12, 2016.
(Continued)

*Primary Examiner* — Daniel W Fowler
(74) *Attorney, Agent, or Firm* — Arent Fox LLP

(57) ABSTRACT

The disclosure relates to three enhancements for a surgical snare: an electrosurgical snare in which the loop of snare wire extends from an energy transfer surface which can act both as a physical reaction surface for mechanical cutting using the snare and as a region for emitting electromagnetic energy; a surgical snare having a snare wire having a first end connected to a movable boss that is slidably mounted on a coaxial cable; and a surgical snare having an end cap with a distally facing reaction surface and a pair of channels for
(Continued)

guiding a snare wire, where the distally facing reaction surface is arranged to contact the retractable loop when fully retracted.

37 Claims, 10 Drawing Sheets

(51) Int. Cl.
    *A61B 18/00*     (2006.01)
    *A61B 18/14*     (2006.01)
    *A61B 17/221*     (2006.01)
    *A61B 18/04*     (2006.01)

(52) U.S. Cl.
    CPC ....... *A61B 18/04* (2013.01); *A61B 2017/2212* (2013.01); *A61B 2018/00077* (2013.01); *A61B 2018/00083* (2013.01); *A61B 2018/00214* (2013.01); *A61B 2018/00494* (2013.01); *A61B 2018/00589* (2013.01); *A61B 2018/00601* (2013.01); *A61B 2018/141* (2013.01); *A61B 2018/183* (2013.01)

(58) Field of Classification Search
    CPC ........... A61B 2018/00077; A61B 2018/00083; A61B 2018/00214; A61B 2018/141; A61B 18/14; A61B 2018/1407; A61B 18/18; A61B 2018/1853; A61B 2018/1861; A61B 2018/144; A61B 18/00–28; A61B 2018/00005–266
See application file for complete search history.

(56) References Cited

U.S. PATENT DOCUMENTS

| 5,989,264 | A | | 11/1999 | Wright | |
|---|---|---|---|---|---|
| 6,016,452 | A | * | 1/2000 | Kasevich | ........... A61B 18/1206 607/101 |
| 2007/0250070 | A1 | | 10/2007 | Nobis et al. | |
| 2009/0036899 | A1 | * | 2/2009 | Carlton | ............ A61B 17/32056 606/113 |
| 2010/0137857 | A1 | * | 6/2010 | Shroff | ................ A61B 18/1815 606/33 |
| 2010/0145328 | A1 | * | 6/2010 | Hancock | ................ A61B 18/18 606/33 |
| 2012/0172865 | A1 | * | 7/2012 | Hancock | ............ H01Q 21/0075 606/33 |
| 2015/0250540 | A1 | * | 9/2015 | Behdad | .................... H01Q 9/42 606/33 |
| 2016/0166314 | A1 | * | 6/2016 | Hancock | ............ A61B 18/1815 606/33 |

FOREIGN PATENT DOCUMENTS

| WO | WO 97/40759 A1 | 11/1997 |
|---|---|---|
| WO | WO 2015/004420 A1 | 1/2015 |

OTHER PUBLICATIONS

International Search Report and Written Opinion of related International Patent Application No. PCT/EP2016/070990 dated Feb. 27, 2017.

\* cited by examiner

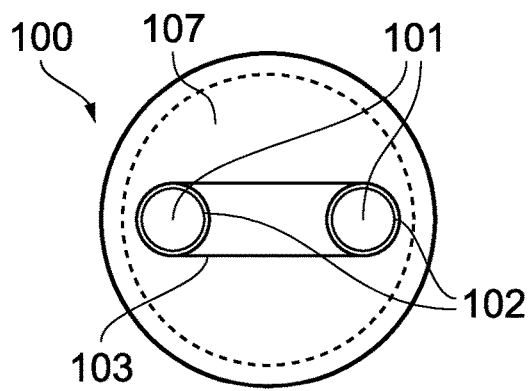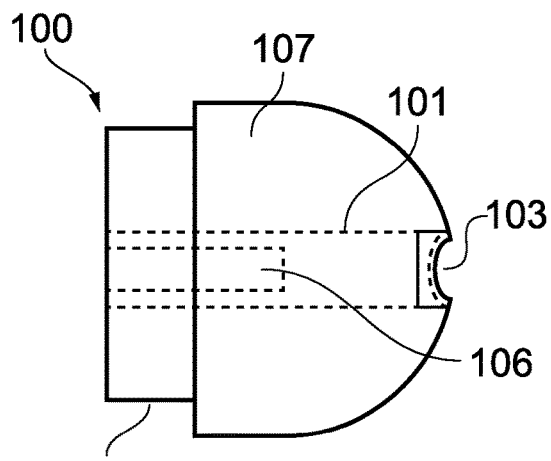
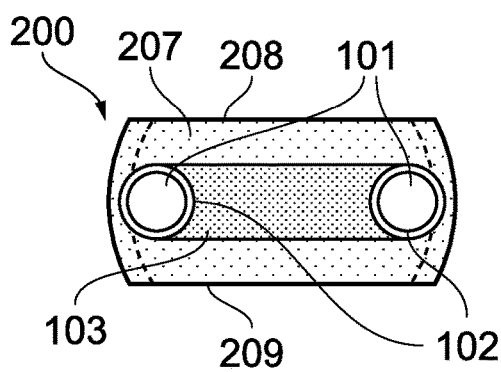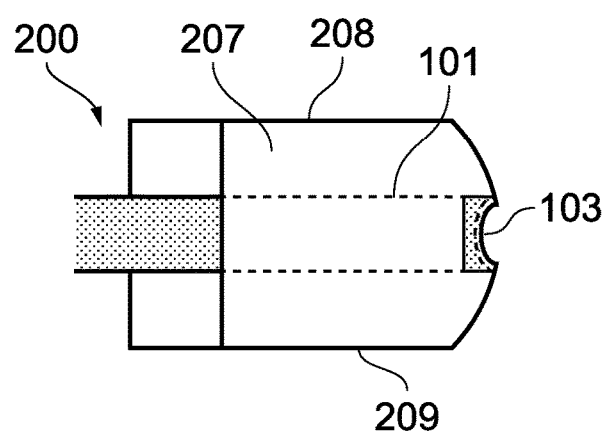
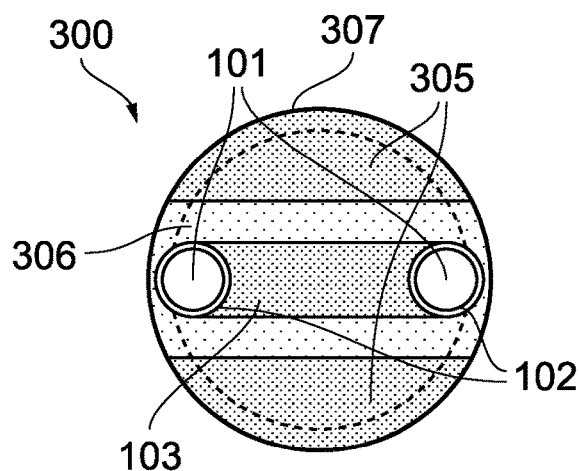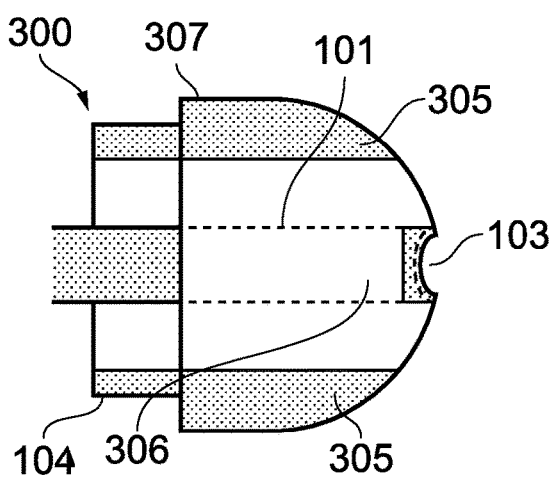

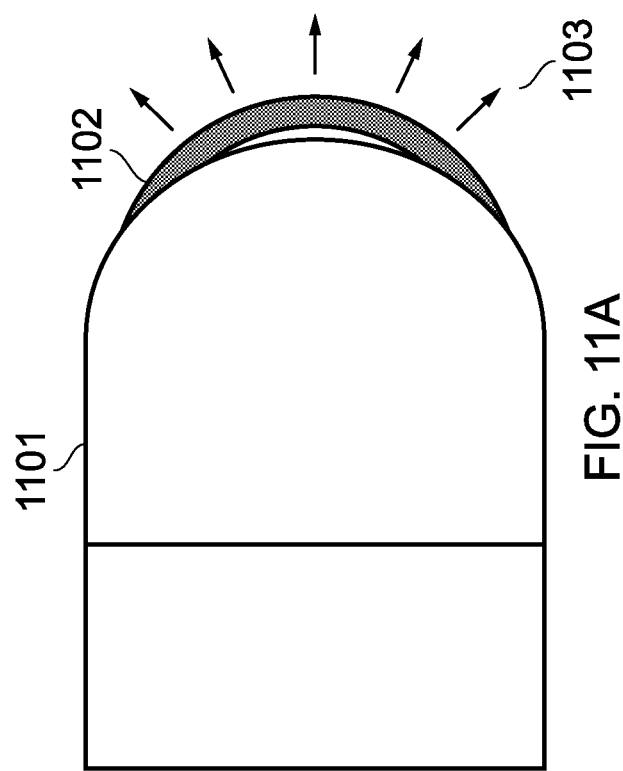
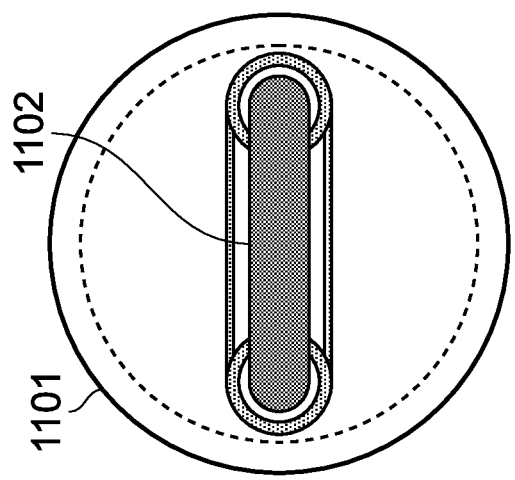
FIG. 11A
FIG. 11B

ELECTROSURGICAL SNARE

CROSS-REFERENCE TO RELATED APPLICATIONS

This application is a National Stage Entry of International Patent Application No. PCT/EP2016/070990, filed on Sep. 6, 2016, which claims priority to British Patent Application No. 1515828.0 filed on Sep. 7, 2015. The disclosures of the priority applications are incorporated in their entirety herein by reference.

FIELD OF THE INVENTION

The invention relates to a surgical snare, e.g. for use in a polypectomy procedure. In particular, the invention may relate to medical snares suitable for insertion down the instrument channel of an endoscope (or any other type of scoping device used in the gastrointestinal (GI) tract or elsewhere in the human or animal body, such as the nasal cavity), and which may include a means for introducing electromagnetic energy into biological tissue.

BACKGROUND TO THE INVENTION

Polyps in the GI tract can be removed using a medical snare in an endoscopic procedure, e.g. using a colonoscope. In the case of pedunculated polyps, the snare is passed over the polyp and tightened around the polyp's neck (or stem), which is then cut and the polyp removed. The cutting process may be performed or enhanced by passing a radiofrequency (RF) current through the biological tissue. The current may also facilitate cauterisation.

Sessile polyps can be removed in a similar manner. It is preferable to "plump up" such polyps before removal by injecting saline or sodium hyaluronate, under the polyp to raise it away from the surrounding colon wall. This may help to reduce the risk of bowel perforation.

WO 2015/004420 discloses an electrosurgical snare in which an electrode was extendable into the loop of the snare.

SUMMARY OF THE INVENTION

The disclosure herein provides three enhancements for a surgical snare instrument. The first enhancement concerns how electromagnetic energy (particularly microwave energy) is delivered to tissue, both when tissue is encircled by a loop of snare wire in an extended configuration and when tissue is located radially outwardly from the loop of snare wire in a retracted configuration. Thus, the snare may be operable in two positions: an open position (corresponding to the extended configuration) and a closed position (corresponding to the retracted configuration). In the open position, the snare may be used to ensnare tissue for excision. In the closed position, the snare may be used as a general purpose haemostat.

The second enhancement relates to means for actuating (i.e. extending and retracting) the snare wire.

The third enhancement relates to the geometry and structure of the distal head assembly from which the loop of snare wire extends.

At its most general, a first aspect of the invention provides an electrosurgical snare in which the loop of snare wire extends from an energy transfer surface which can act both as a physical reaction surface for mechanical cutting using the snare and as a region for emitting electromagnetic (e.g. microwave or RF) energy.

According to the first aspect of the invention, there is provided a surgical snare comprising: a coaxial cable having an inner conductor, an outer conductor and a dielectric material separating the inner conductor from the outer conductor; a distal head assembly disposed at a distal end of the coaxial cable; and a snare wire mounted in the distal head assembly, wherein the distal head assembly comprises an end cap having: a distally facing energy transfer structure that is connected to the inner conductor, and a pair of channels, each of the pair of channels extending axially between an outlet on the distally facing energy transfer surface and an inlet on a proximal surface of the end cap, wherein the snare wire is disposed within the pair of channels to form a retractable loop beyond the distally facing energy transfer surface. The coaxial cable may be arranged to deliver electromagnetic energy to the distal head assembly. The distally facing energy transfer structure may be configured to transmit the electromagnetic energy conveyed to the distal head assembly by the coaxial cable into biological tissue at the distal head assembly.

The coaxial cable may be arranged (e.g. appropriately dimensioned) to convey microwave electromagnetic energy, wherein the energy transfer structure may be configured as an antenna for radiating microwave electromagnetic energy. The antenna can be formed of an electrically conductive material, or a microwave ceramic or similarly low-loss dielectric that enables the effective propagation of microwave energy.

The coaxial cable may be arranged to convey radiofrequency (RF) electromagnetic energy. The RF energy may be conveyed by the same coaxial cable as the microwave energy. The RF energy and microwave energy may be conveyed separately or simultaneously. If the energy transfer structure is to transmit RF energy, it may comprise an electrically conductive material electrically connected to the inner conductor. For example, the energy transfer structure may comprise an electrically conductive surface formed on the end cap.

The snare wire may comprise an electrically conductive material electrically connected to the outer conductor and preferably electrically insulated from the inner conductor and the energy transfer structure. The energy transfer structure may act as an active electrode and the snare wire may act as a return electrode. In order to isolate the electrically conductive surface (i.e. active electrode) from the snare wire (i.e. return electrode), insulating material can be provided inside of the channels to prevent shorting between the inner and outer conductors.

If the device is configured to use microwave electromagnetic energy only, it may not be necessary for the snare wire and conductive surface are insulated. For example an H-field loop may be used to ensure efficient propagation of the microwave energy.

The configuration of the snare wire and distally facing energy transfer structure in combination may act to ensure that the delivered energy goes into tissue encircled by the retractable loop. In use, the electromagnetic energy may be used to coagulate tissue that is grasped by the retractable loop and/or to assist in the cutting operation. When the retractable loop is retracted, the energy can be delivered outwardly and away from the distal end of the head assembly. In the retracted state, the loop may have a diameter of between 5 mm and 0.5 mm. In this manner, the device can be used to "spot" coagulate the area around a polyp stalk to stem blood flow before beginning a polypectomy procedure. The device may be used in this retracted configuration to coagulate vessels in the bowel or around an area where the polyp stalk is to be removed. Alternatively or additionally, the device may be used in the retracted configuration to mark out a region around a sessile polyp or tumour.

The snare wire may be slidably mounted in the distal head assembly, whereby the loop is retractable towards the energy transfer structure. The retractable loop may be arranged to contact the energy transfer structure when fully retracted. The energy transfer structure may therefore act as a reaction surface for a physical force applied by the snare wire.

The end cap may comprise an electrically conductive body electrically connected to the inner conductor. In other words, the end cap may comprise a single solid conductive mass that provides both the proximal surface and a distally facing conductive surface that is the energy transfer structure. The pair of channels may be holes formed (e.g. bored or drilled) through the electrically conductive body. The channels may be parallel to each other and aligned with the axis of the device (e.g. the axis of the coaxial cable). The holes may be arranged symmetrically with respect to the axis. However it will be understood that the arrangement of the holes may vary, e.g. according to the specific application of the device. The holes may have an insulating layer on their inner surfaces to electrically insulate the snare wire from the electrically conductive body. Alternatively or additionally the snare wire itself may have an insulating cover along the portions which pass through the channels during normal operation. The end cap may be coated with an insulating and/or non-stick layer of material to prevent coagulated tissue sticking to the radiator. This insulating material may be, for example, a layer of Parylene C, PTFE, Teflon, or a material with similar properties. It may also be preferable that the loop of the snare wire is coated with a thin layer of insulating and/or non-stick material to a thickness of, for example, 10 μm or less.

As discussed above, the distally facing energy transfer structure may provide a reaction surface for contacting the retractable loop when fully retracted. In other words, the area encircled by the loop may be reduced to zero as it is retracted. The reaction surface may be a portion of the distally facing energy transfer structure that extends between the outlets of the pair of channels. The reaction surface may be flat. However, preferably the reaction surface is curved to fit against the snare wire as it is retracted. The reaction surface may have a range of radii of curvature, e.g. from 1 mm to 10 mm. For example, the reaction surface may resemble a portion of a conical or cylindrical surface. The reaction surface may include or comprise a recess on the energy transfer structure.

The reaction surface may include a cutting feature, e.g. sharpened edge or blade, to facilitate cutting of the biological tissue captured by the snare wire. The cutting feature may be provided inside the recess discussed above so that it does not protrude from the reaction surface. This configuration reduces the risk of perforation or unwanted tissue damage if the device is pushed against the wall of the bowel, oesophagus or other organ.

If the energy transfer structure includes an electrically conductive surface, the reaction surface may comprise a strip of insulating material across the distally facing conductive surface to avoid creating an electrical connection between the distally facing conductive surface and the snare wire. The strip may be formed separately from the end cap and attached, e.g. bonded later. For example, the end cap may have a recess formed across it for receiving the strip. The reaction surface may be a groove in the distally facing conductive surface. For example, the strip of insulating material may be formed in a concave manner to cooperate with the cross-section profile of the snare wire. The strip may be a thin microstrip line or the like.

The distally facing conductive surface may be rounded, e.g. in a hemispherical or dome-like manner. This shape may assist in delivery of the electromagnetic energy and may also provide a smooth surface to prevent accidental snagging on tissue. The distally facing conductive surface may be a dome, wherein the outlets of the pair of channels are located on the dome. In other words, the retractable loop extends out from the radiating surface of the instrument rather than having a separate radiating element that is insertable into the area encircled by the loop.

In order to focus the electromagnetic energy into the area encircled by the retractable loop, and to prevent the electromagnetic energy from entering healthy tissue surrounding the instrument, the end cap may have insulating cover portions on its side surfaces that are aligned with the plane of the retractable loop. In other words, portions of the end cap that lie above and below the retractable loop do not present an outward conductive surface.

The snare wire may be connected to the outer conductor of the coaxial cable at a proximal end of the distal head assembly. In one example, a joint that connects one end of the snare wire to the outer conductor also serves as a fixed anchor point for the snare wire. Thus, the distal head assembly may include a fixed boss mounted on the coaxial cable and electrically connected to the outer conductor, wherein the snare wire is electrically connected to the fixed boss. The fixed boss may be a conductive (e.g. metal) ring clamped onto the outer conductor at the proximal end of the distal head assembly. The snare wire may be soldered to the fixed boss. Alternatively the snare wire can be secured to the cap using an interference fit or a threaded connection in one of the channels.

A first end of the snare wire may be connected to a push rod that is axially slidable relative to the coaxial cable, and a second end of the snare wire may be attached to the fixed boss. Movement of the first end forwards and backwards along the coaxial cable causes the retractable loop to extend and retract. In order to maintain alignment of the retractable loop, the first end of the snare wire may be connected to a movable boss that is slidably mounted on the coaxial cable. The movable boss may be a sleeve that slides over the coaxial cable. This configuration may help to prevent uncontrolled movement of the snare wire loop by restricting the snare wire to a plane generally parallel with the plane of the loop.

Alternatively, the second end may also be movable e.g. simultaneously with the first end. For example, the second end may be connected to the push rod, e.g. via the moveable boss. Or the first and second ends of the snare wire may be joined to each other to form a common wire, which is movable. For example, the common wire may be connected to the movable boss or push rod which is axially slidable relative to the coaxial cable.

The distal head assembly may include an impedance transformer portion (also referred to herein as 'transformer portion') mounted between a distal end of the coaxial cable and the end cap, the transformer portion being arranged to match the impedance of the coaxial cable to the impedance of the end cap. This is useful if the impedance of the end cap is not the same as the impedance of the coaxial cable. The transformer portion may be arranged to act as a quarter wave impedance transformer.

The transformer portion may include a length of electrically conductive material extending axially between a distal end of the inner conductor and the proximal surface of the end cap, and a pair of passages that extend axially on opposing sides of the length of electrically conductive material, wherein the snare wire passes through the pair of passages. Preferably the passages are lined with an insulator, thereby isolating the snare wire from the inner conductor. These passages help to prevent the wire buckling or moving in an uncontrolled fashion. The axial length of this structure may be chosen in conjunction with its impedance to provide the required impedance match.

The surgical snare may have a sleeve (e.g. an electrically insulating sheath) arranged to enclose side surfaces of the distal head assembly. In other words, the sleeve may enclose the coaxial cable, push rod, transformer portion and parts of the snare wire other than the retractable loop.

In an embodiment, a distal end of the sleeve may be attached (e.g. bonded) to a proximal peripheral edge of the end cap or reaction surface. The snare wire may thus be movable relative to both the end cap and the insulating sheath to extend and retract the retractable loop. In this embodiment the snare wire may be fixed relative to the instrument channel of the endoscope through which the surgical snare is introduced. The surgical snare is therefore operable by moving the insulating sheath.

Alternatively, the sleeve may be slidable relative to the distal end assembly so as to enclose the loop of the snare wire. In one embodiment, the retractable loop may be fixed relative to the end cap, and the diameter of the loop may be reduced (i.e. the loop may be retracted) by sliding the sleeve over it.

The sleeve may have an internal longitudinal partition which separates an internal volume of the sleeve into a first longitudinal cavity for carrying the coaxial cable and a second longitudinal cavity for carrying a push rod that is connected to the snare wire. The push rod may be a tube or sheath mounted around the co-axial cable and slidable relative to it.

The manner in which the snare is actuated in the first aspect above may be a second aspect of the invention. According to the second aspect, there is provided a surgical snare comprising a coaxial cable having an inner conductor, an outer conductor and a dielectric material separating the inner conductor from the outer conductor; a distal head assembly disposed at a distal end of the coaxial cable, the distal head assembly having an end cap that is electrically connected to the inner conductor; and a snare wire slidably mounted in the distal head assembly to form a retractable loop beyond the end cap, wherein a first end of the snare wire is connected to a movable boss that is slidably mounted on the coaxial cable.

As discussed above, the snare wire may comprise an electrically conductive portion that is electrically connected to the outer conductor. This connection may be made at an opposite end of the snare wire to where the snare wire is connected to the moveable boss. However the snare wire may be electrically connected to the outer conductor at any suitable point, for example via the moveable boss. As with the first aspect, the snare wire may be electrically insulated from the inner conductor if the device is to be configured for use with RF electromagnetic energy. Providing a movable boss on the coaxial cable assists in maintaining a secure spatial relationship between the snare wire and the coaxial cable, which can prevent the snare wire from twisting in use.

Features of the first aspect mentioned above may also be provided in the second aspect. For example, the distal head assembly may include a fixed boss mounted on the coaxial cable, and wherein a second end of the snare wire is attached to the fixed boss. The fixed boss may be electrically connected to the outer conductor.

However, in an alternative arrangement, a second end of the snare wire may also be attached to the movable boss. This means both sides of the snare wire move when the movable boss slides along the coaxial cable. This can assist in shortening the length of the instrument, since the movable boss only needs to traverse half the distance along the coaxial cable to achieve the same size loop as an arrangement in which only one end of the snare wire is attached to the movable boss. This alternative may also provide a more evenly distributed cutting force at the end cap (i.e. at the reaction surface).

In a further alternative arrangement, a second end of the snare wire may be joined with the first end of the snare wire between the fixed boss and the moveable boss. In this arrangement the second end may pass through the fixed boss before connecting to the first end. Again, this can assist in shortening the length of the instrument and provide the other advantages discussed above.

The movable boss may be operated using a push rod or the like. In an embodiment, the push rod is a sleeve mounted around and slidable relative to the coaxial cable. This configuration may provide the user with more control over the movement of the snare because the coaxial cable is less susceptible to bending or twisting than a separate thin rod.

As discussed above with relation to the first and second aspects of the invention, the loop may be retracted into an almost or completely retracted position in which it abuts or is very close to the reaction surface. When the loop is in the almost or completely retracted configuration, the device is useable in an alternative mode in which energy is delivered away from the end cap and into tissue which the device is near or abuts. Such a mode can be used to apply electromagnetic energy to points of tissue not encircled by the loop i.e. the device may be used as a point applicator. For example, before a polyp is removed, it is desirable to inhibit blood flow in the area around the stem. The device may be used in this alternative mode to apply electromagnetic energy to the bleeding tissue so as to aid coagulation in this region. The device may also be used to stop any residual bleeding following the removal of the polyp. In this situation, the loop will be pulled into the reaction surface and the device will be used as a point applicator in order to aid coagulation with the distal end of the snare-wire functioning as a microwave energy radiating antenna.

Thus, the coaxial cable can be connected (e.g. at its proximal end) to a suitable generator to receive microwave energy. The retractable loop may be movable between an extended configuration for delivering the microwave energy to tissue encircled by the snare wire and a retracted configuration for delivering microwave energy outwardly from a distal exposed portion of the snare wire, i.e. a portion of the snare wire that is not inside the end cap when retracted. The snare wire may be fully retracted, i.e. in contact with the distally facing conductive surface, when the retractable loop is in the retracted configuration. Alternatively, there may be a small gap between the snare wire and the distally facing conductive surface when the retractable loop is in the retracted configuration.

The geometry of the end cap may be a third aspect of the invention. This aspect may be used in both electrosurgical snares, where electromagnetic energy is supplied, and in "cold" snares, where only mechanical cutting is performed. According to the third aspect of the invention, there is provided a surgical snare comprising: a distal head assembly; and a snare wire slidably mounted in the distal head assembly, wherein the distal head assembly comprises an end cap having: a distally facing reaction surface, and a pair of channels, each of the pair of channels extending between an outlet on the distally facing reaction surface and an inlet on a proximal surface of the end cap, wherein the snare wire is disposed within the pair of channels to form a retractable loop beyond the distally facing conductive surface, and wherein the distally facing reaction surface is arranged to contact the retractable loop when fully retracted. The pair of channels may extend parallel to each other. They may extend in an axial direction through the end cap. As discussed above with respect to the first aspect, it may be desirable to include a small blade on or in the end cap to cut through the tissue, e.g. following application of microwave energy if available. Ideally, the blade should not protrude from the end cap, otherwise this presents a risk of damage to the wall of the colon or perforation due to the device being pushed against the wall of the bowel (or another organ).

Features of the first and second aspects mentioned above may also be provided in the third aspect. For example, the distally facing reaction surface may include a groove for receiving the retractable loop, and the distally facing reaction surface may be rounded, i.e. convex in the distal direction.

The surgical snare described herein may be used in a polypectomy procedure. The retractable loop can be passed around the stem of polyp, which is then cut from the gut wall by the application of electrical and/or mechanical energy. Advantageously, the distally facing conductive surface forms a part of the boundary of the retractable loop, thereby reducing the chance of snagging the conductive dome on any tissue.

This device could also be used as a general purpose microwave haemostat when the loop is fully retracted. In this configuration, the microwave radiation will be emitted from the end cap and full retracted loop.

Herein, "microwave energy" may be used broadly to indicate an electromagnetic energy in a frequency range of 400 MHz to 100 GHz, but preferably in a range of 1 GHz to 60 GHz, more preferably 2.45 GHz to 30 GHz or 5 GHz to 30 GHz. The invention may be used at a single specific frequency, such as any one or more of: 915 MHz, 2.45 GHz, 3.3 GHz, 5.8 GHz, 10 GHz, 14.5 GHz and 24 GHz.

Herein, radiofrequency (RF) may mean a stable fixed frequency in the range 10 kHz to 300 MHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz.

The surgical snare of the invention may be configured for insertion down an instrument channel of an endoscope, gastro scope, etc., or may be arranged for use in laparoscopic surgery or in natural orifice translumenal endoscopic surgery (NOTES), transanal endoscopic microsurgery (TEMS), or transanal submucosal endoscopic resection (TASER) procedures or in a general open procedure. The diameter of the instrument channel in the endoscope may be 2.2 mm, 2.8 mm, 3.2 mm or larger. The maximum width of the structures discussed herein may thus be set to be lower than one or more of these dimensions.

BRIEF DESCRIPTION OF THE DRAWINGS

Embodiments of the invention are described in detail below with reference to the accompanying drawings, in which:

FIGS. 1A and 1B show respectively a front-on and side-on schematic view of a conductive cap for a surgical snare that is an embodiment of the invention;

FIGS. 2A and 2B show respectively a front-on and side-on schematic view of a truncated conductive cap for a surgical snare that is another embodiment of the invention;

FIGS. 3A and 3B show respectively a front-on and side-on schematic view of a truncated conductive cap for a surgical snare with insulating portions that is another embodiment of the invention;

FIGS. 11A and 11B show respectively a top-down and end-on schematic view of the end of a surgical snare that is an embodiment of the invention, when the snare wire is retracted;

DETAILED DESCRIPTION; FURTHER OPTIONS AND PREFERENCES

Figure 4:
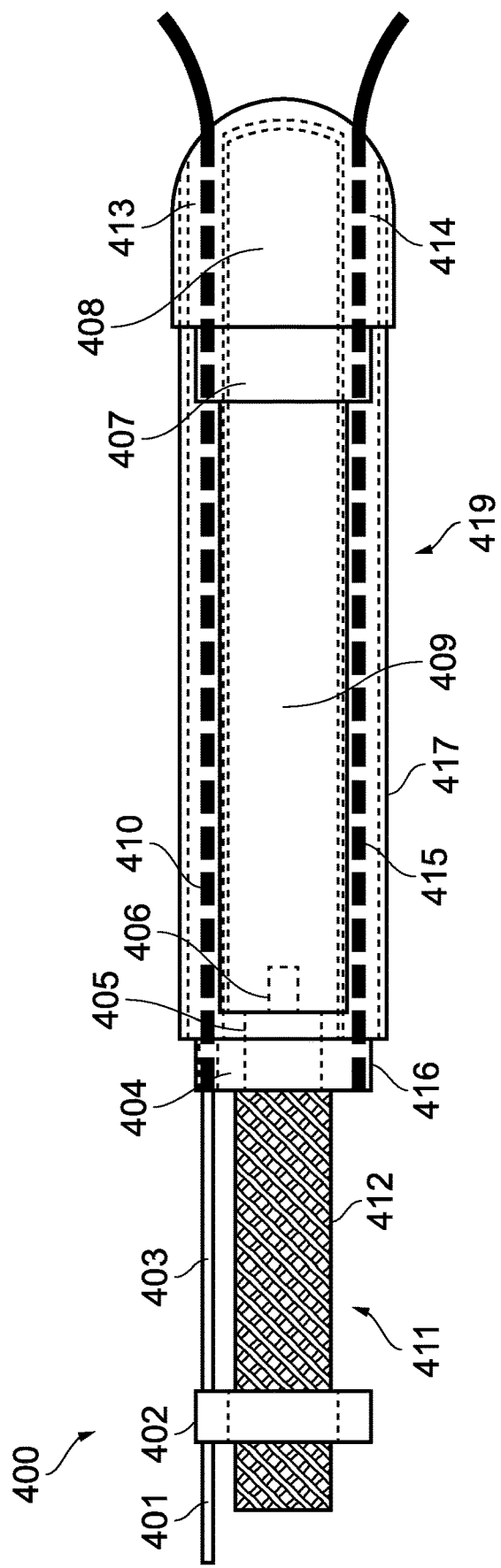
FIG. 4 shows a cross-sectional top-down view of a surgical snare which is another embodiment of the invention.

FIG. 1A shows a front-on view of a distal end cap 100 for use on a surgical snare. As explained below, the distal end cap is suitable for use with both electrosurgical snares, in which RF or microwave energy is delivered to assist the cutting operation, and purely mechanical snares (sometimes referred to as "cold" snares), in which no additional energy is supplied. In this embodiment, the end cap 100 is formed from a single piece of electrically conductive material, but the invention is not limited to this arrangement. For example, the end cap 100 may be formed of a microwave ceramic or another suitable dielectric that is able to transmit microwave electromagnetic energy. In this example, the end cap 100 has a round proximal face which smoothly curves in the distal direction to form a tip 107, which resembles a dome. In this example the tip 107 had a diameter of 2.4 mm. The tip 107 has two channels 101 passing through it, which act as guides for two ends of a loop of wire which forms the snare. Each channel has an inlet at the proximal surface and an outlet at the distal surface of the tip 107. In this example, the channels 101 each have a diameter of 0.7 mm. The channels 101 are both lined with an electrical insulator 102 such that the interior of each channel 101 is electrically isolated from the tip 107. In practice this means that the snare wire passing through the channels 101 is electrically insulated from the electrically conductive material of the end cap 100.

In this example, the channels 101 have a circular cross-section. The shape of the cross-section of the channels may be the same shape as the cross-section of the snare wire. This shape may be non-circular, e.g. triangular, rectangular, etc.

In an embodiment, the snare wire may be fixed relative to the distal end cap 100. In other words a fixed length of snare wire may extend in a loop beyond the distally facing surface of the end cap. In such an embodiment, the loop may be retracted (i.e. the area encircled by the loop may be reduced) by sliding a sleeve over the end cap and loop.

In another embodiment, the snare wire may be slidably mounted in the distal end cap 100. The cross-sectional area of the snare wire may be less than the cross-sectional area of each channel so that there is enough play to permit the snare wire to slide through the channel.

A groove 103 may be formed between the two channels 101 on the front (distal) surface of the tip 107. The groove 103 may be shaped to receive the snare wire as it is pulled against the tip 107. Groove 107 may be less than 1 mm deep to 10 mm deep. The groove 103 may therefore represent a reaction surface against which a mechanically cutting force is applied to tissue (e.g. a polyp stem) that is disposed within the loop of the snare. In some embodiments, the groove 103 may be provided with a blade or other sharp surface to facilitate or improve the cutting action. The groove 103 may have a layer of electrically insulating material disposed therein to maintain electrical isolation between the snare wire and tip 107 even when the loop is fully closed. When the loop is fully closed, it may form a continuous surface, i.e. one without a gap between the loop and the groove 103, and act as a general purpose microwave coagulator or haemostat.

FIG. 1B shows the end cap 100 in a side-on view. Here it can be seen that tip 107 presents a distally facing convex surface, whereas the groove 103 is a distally facing concave indentation. It may be desirable to make the concave ends sharp or rounded. In the former, the wire will prevent it cutting the bowel wall in the manner discussed above.

The end cap 100 also may have a recess 106 extending in a distal direction from the proximal surface. The recess 106 is shaped to receive a signal feed (e.g. a portion of an inner conductor of a coaxial cable that protrudes beyond the coaxial cable's outer conductor and dielectric material). This is discussed below in more detail with reference to FIG. 6. In this embodiment, the inner conductor recess 106 is situated generally midway between the channels 101, but the invention is not limited to this configuration.

An annular recess 104 is formed around the periphery of the proximal surface. The annular recess 104 is arranged to receive and be attached (e.g. bonded) to the distal edge of a sleeve (not shown). This is discussed below in more detail with reference to FIG. 6.

FIG. 2A shows a front-on view of another embodiment of a distal end cap 200 for a surgical snare. The end cap 200 shares a number of features with the end cap 100 shown in FIG. 1A, and so the same reference numerals are used to label corresponding parts. The end cap 200 has a tip 207, which is electrically conductive and, as with cap 100, the tip 207 is curved to partially form a dome. In contrast with the tip 107 of cap 100 shown in FIG. 1A, however, the tip 207 is truncated so as to form flat surfaces at the top 208 and bottom 209 of the tip 207. The tip 207 of the cap 200 then has a smaller profile than the tip 107 of the first cap 100. In this example, the cap 200 had a thickness of 1.4 mm. This allows any undesirable loss of energy into the wall of the bowel to be minimised, as the contact between the cap 200 and the wall of the bowel can be reduced. FIG. 2B shows a side-on view of the cap 200, which illustrates the truncation of the tip 207.

FIG. 3A shows a front-on view of another embodiment of a distal end cap 300 for use in a surgical snare. Again, this end cap 300 shares a number of features with the end caps 100, 200 shown in FIGS. 1A, 1B, 2A and 2B, and so the same reference numerals are used for corresponding features.

In this example, the end cap 300 has a tip 307 formed of two portions: a conductive portion 306, which has the same form as the truncated tip 207 of the cap 200; and an insulating portion 305, which is attached to the flat upper and lower surfaces of the conductive portion 306. The outer profile of the insulating portion 305 is shaped to form a dome at the distal end of the cap 300 similar to the dome in FIGS. 1A and 1B. FIG. 3B shows a side-on view of the cap 300, which illustrates the dome formed of the conductive portion 306 and insulating portion 305.

The end caps discussed may be made of different materials depending on the specific application required. For example, it may be important that the end cap be sufficiently biocompatible (i.e. have a known host response in a particular situation). Therefore the end cap may be made of platinum, platinum iridium, gold, tantalum or a mixture thereof. Where the end cap is made of a metal, the device may be used in fluoroscopic procedures as the end cap is then opaque to x-rays. In order to prevent tissue sticking, as discussed above the end cap may have an outer coating (not shown) of Teflon, PTFE or Parylene C.

FIG. 4 shows a top-down cross-sectional view of a surgical snare 400 that is another embodiment of the invention. In this example, the surgical snare may be dimensioned for endoscopic use. For example, the largest width (i.e. the diameter of the distal end cap) of the device is less than 2.6 mm, and may be around 1.4 mm, in order to make it suitable for passing through the instrument channel of an endoscope or any other type of surgical scope.

The surgical snare 400 comprises a coaxial cable 411 and a distal head assembly 419 connected to the distal end of the coaxial cable 411. The coaxial cable has an inner conductor 406, an outer conductor 412, and a dielectric 405 separating the inner conductor 406 from the outer conductor 412. The coaxial cable 411 may typically have an impedance of around 50 ohms. For example, it may be a Sucoform® 47 or Sucoform® 86 cable from Huber & Suhner.

The outer conductor 412 terminates within a fixed boss 404 at the proximal end of the distal head assembly 419. The fixed boss 404 comprises an electrically conductive element that is electrically connected to the outer conductor 412. The fixed boss may be an electrically conductive ring element that is clamped or otherwise secured to the outer conductor 412 of the coaxial cable 411.

A movable boss 402 is slidably mounted on the coaxial cable 411 proximally to the fixed boss 404. In this embodiment, the movable boss is a ring that fits around the outer conductor 412. The outer conductor 412 may have a lubricious coating or may be encased in a suitable sheath (not shown) to reduce friction or prevent the braid of the outer jacket of the co-axial cable becoming troublesome. The ring may have an outer diameter of 2.4 mm and an inner diameter of 2.2 mm so as to fit around the coaxial cable and within the instrument channel of an endoscope, in some examples the ring may have an outer diameter of 1.4 mm. The outer diameter of the ring is generally dependent on the dimensions of the instrument channel of the endoscope the device is to be used in. The movable boss 402 has a push rod 401 attached to it. The push rod 401 may extend through the instrument channel of the endoscope, whereby the movable boss 402 can be moved axially relative to the coaxial cable, e.g. to vary the distance between the movable boss 402 and the fixed boss 404. This mechanism is used to extend and retract the snare, as explained below.

The distal head assembly 419 comprises a distal end cap 408 connected to the coaxial cable 411 by a transformer portion 409 to match the impedance of the cable (the characteristic impedance) to that of the tissue load. The distal end cap 408 may be any of the caps discussed with reference to FIGS. 1A and 1B or FIGS. 2A and 2B or FIGS. 3A and 3B. In other words the distal end cap 408 comprises an electrically conductive body or a low loss dielectric, e.g. a microwave ceramic, having a pair of channels 413, 414 extending therethrough from a proximal surface to a curved (dome-like or hemispherical) distal surface. The pair of channels 413, 414 are preferably aligned with each other in the axial direction, and are preferably arranged symmetrically with respect to the axis of the device. The pair of channels 413, 414 are arranged to convey a snare wire 403 as discussed below. If the distal end cap 408 comprises an electrically conductive body, the inside surface of the pair of channels 413, 414 has a layer of insulating material formed thereon to electrically insulate the snare wire 403 from the electrically conductive body.

The transformer portion 409 comprises a length of electrically conductive material which provides an electrical connection between the inner conductor 406 of the coaxial cable 411 and the electrically conductive body of the distal end cap 408. In this embodiment, the length of electrically conductive material has a cuboidal shape with a recess formed in a proximal face thereof for receiving an exposed length of the inner conductor 406. However, the invention is not be limited to this geometry. The physical length of the electrically conductive material may be such that it has an electrical length equal to an odd multiple of a quarter wavelength at the frequency of choice. A distal face of the length of electrically conductive material may abut the electrically conductive body of the distal end cap to provide the electrical connection. Alternatively the electrically conductive material may be integral with the electrically conductive body of the distal cap, thereby forming a single electrically conductive body.

A pair of axially extending insulated passages 410, 415 are located on opposing sides of the transformer portion 409. The pair of insulating passages convey the snare wire 403 to the distal end cap 408 as discussed in more detail below.

In this embodiment, the transformer portion 409 and pair of axially extending insulated passages 410, 415 are enclosed in a protective insulating sheath 417, which has a distal end secured (e.g. bonded) to a proximal portion 407 of the distal end cap 408 and a proximal end secured (e.g. bonded) to the fixed boss 404. The insulating sheath 417 may be made from polytetrafluoroethylene (PTFE) or polyether ether ketone (PEEK) or the like. These materials may also be used to coat the end cap to prevent tissue sticking. Other materials such as Parylene N, C or D may also be used.

As mentioned above, the outer conductor 412 of the coaxial cable 411 terminates within the fixed boss 404. However, the dielectric material 405 and the inner conductor 406 protrude beyond the distal termination of the outer conductor 412 and extend axially inside the insulating sheath 417. The dielectric material 405 terminates at the distal face of the transformer portion 409, while the inner conductor 406 protrudes further beyond the distal termination of the dielectric material and extends into the recess formed in the proximal face of the transformer portion 409. In this example, the inner conductor 406 is soldered into a 0.35 mm diameter hole in the length of electrically conductive material.

A snare wire 403 has a first end fixed to the movable boss 402. The snare wire 403 extends from the movable boss 402 towards and through the fixed boss 404 to enter the distal head assembly 419. The snare wire 403 extends through the first insulating passage 410 into the first channel 413 to exit the distal end cap 408. The snare wire 403 forms a loop (not shown), preferably a nibless loop, around a region beyond the distal end cap 408 and then returns into the distal end cap 408 via the second channel 414. The snare wire 403 extends through the second channel 414 into and through the second insulating passage 415 until it reaches the fixed boss 404. The snare wire 403 has a second end that is connected both physically and electrically. In this arrangement the snare wire is connected by a soldered joint 416, however the connection could be through crimping, welding, or another means that ensures a physical and electrical connection to the fixed boss 404 at the proximal end of the second insulating passage 415. Since the fixed boss 404 (or a portion of it) is electrically connected to the outer conductor 412 of the coaxial cable 411, the snare wire is also electrically connected to the outer conductor 412 of the coaxial cable 411. The insulating material of the insulating passages 410, 415 and the channels 413, 414 prevent the snare wire 403 from contacting portions of the device that are electrically connected to the inner conductor 406 of the coaxial cable.

The snare wire 403 is made of any suitable electrically conductive material such as nickel titanium (also known as nitinol), and in this embodiment has a diameter of 0.3 mm. In some applications, the snare wire 403 is made of nitinol which has shape memory properties. In other examples, the snare wire 403 may be made of platinum, a platinum and iridium alloy, or gold-plated tungsten. The snare wire 403 can be plated, for example with gold or silver, to reduce the resistance of the core of the snare wire in order to assist effective propagation of the microwave signals. The snare wire 403 with a diameter of 0.3 mm, when present in the insulated passages 410, 415, forms a transmission line with an impedance of around 36 ohms.

In use, when the movable boss 402 is slid towards the fixed boss 404, the snare wire 403 passes through the fixed boss 404 and the length of the snare wire 403 which protrudes from the end cap 408 is increased. This has the effect of increasing the radius of the snare loop. Likewise, sliding the movable boss 402 away from the fixed boss 404 reduces the amount of snare wire 403 which protrudes from the end cap 408, thereby reducing the radius of the snare loop.

If the snare wire 403 is electrically connected to the fixed boss 404 both at the solder joint 416 and as it enters the distal head assembly, a pair of parallel transmission lines exist, each having an impedance of around 72 ohms. Using this fact, the length of the insulating guides 415 and 410 can be chosen to provide a quarter-wave transformer.

In some examples, the snare wire 403 is not soldered to the fixed boss 404 at any point, instead the fixed boss 404 has channels through it with a sufficiently tight diameter (e.g. 0.3 mm) that the snare wire 403 will be in electrical contact with it, without any solder. In examples such as this, the snare wire 403 may extend as two strands, each strand optionally passing through the ring 402, which can be attached to a common push rod.

In this example, the length of electrically conductive material in the transformer portion 409 may be 0.8 mm thick, 1.6 mm wide, and 12.5 mm long. The bulk of the transformer portion 409 may be made of any suitable material, e.g. metal or plastic so long as an electrically conductive path is formed from the inner conductor 406 to the end cap 408. The transformer portion 409 should also be fairly rigid as it acts as a structural member of the device to resist compression or buckling. It may be flexible to an extent, so as to facilitate passing the device down an endoscopic channel. The insulated passages 410, 415 may be formed wholly or partially within the length of electrically conductive material. For example, each of the side edges of the length of electrically conductive material may have a semi-cylindrical recess formed therein. The insulated passage 410, 415 may thus sit flush with the length of electrically conductive material. The insulated passages 410, 415 may have a diameter of 0.7 mm.

The transformer portion 409 functions as a quarter-wave transformer for microwave energy transmitted through the coaxial cable 411. It does this by having a length which is substantially one quarter or an odd multiple thereof of the wavelength of the microwave radiation to be transmitted into the tissue.

Microwave energy (e.g. having a frequency of 5.8 GHz) may be delivered to the surgical snare 400 from a suitable electrosurgical generator (not shown) connected to a proximal end of the coaxial cable 411 (e.g. outside the endoscope). The exposed conductive part of the distal end cap 408 functions as a microwave antenna (preferably a radiating monopole antenna) to radiate microwave energy supplied to it from the coaxial cable 411.

In use, the snare loop would encircle a polyp stem, the operator then reduces the radius of the snare loop by moving the push rod 401 away from the fixed boss 404. The polyp stem is then brought into contact with the conducting portion 107, 207, 306 of the cap 408 and preferably the cutting groove 103 of the cap 408. In this configuration, the microwave energy supplied to the surgical snare 400 can enter the polyp stem, where it will promote coagulation and therefore assist in the removal of the polyp stem or prevent bleeding which would otherwise occur if mechanical action only was employed.

The total length of the surgical snare 400 from movable boss 402 to the end of the cap 408 was approximately 17.2 mm.

Figure 5:
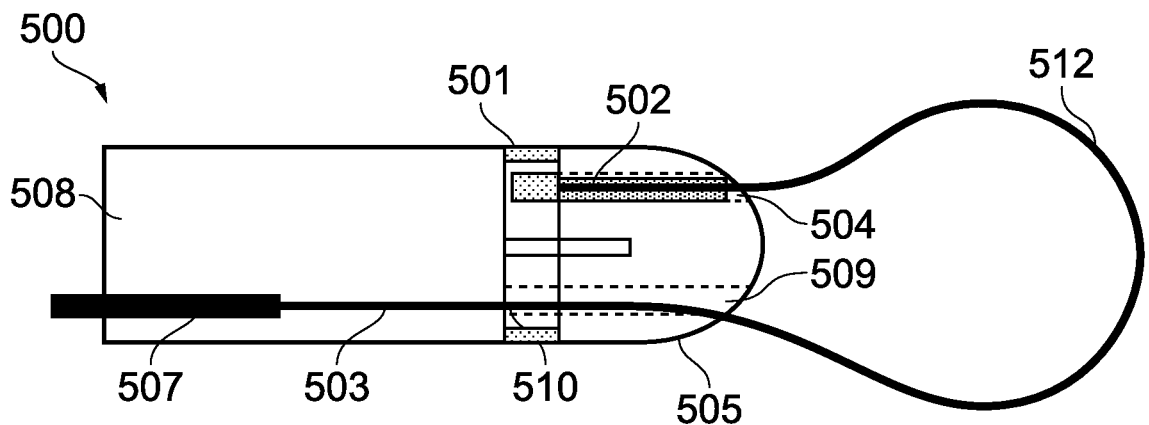
FIG. 5 shows a cross-sectional top-down view of a surgical snare used without an energy supply.

FIG. 5 shows a cross-sectional view of a surgical snare 500. The surgical snare 500 comprises a sleeve 508, which is connected to a cap 505 via a joint 501. The cap 505 illustrated in FIG. 5 is the cap 100 shown in FIGS. 1A and 1B.

As with the surgical snare shown in FIG. 4, a push rod 507 extends from the operator end of the endoscope to the surgical snare 500 through the instrument channel of the endoscope. The push rod 507 in this embodiment however is directly connected to the snare wire 503. The snare wire 503 extends inside the sleeve 508, and through the joint 501. The portion 510 of the snare wire 503 passing first through the joint 501 is freely moveable within the joint 501. The snare wire 503 then extends through a channel 509 of the cap 505 until it extends freely from the cap 505. The snare wire 503 then forms the snare loop 512, by passing into a second channel 504 of the cap 505. A portion 502 of the snare wire 503 is secured within the second channel 504 via a weld (this could also be a crimp or glue bond). In other examples of the device other fixing means can be used; for example a mechanical clamp or forming a taper in the channel 504. Therefore, when the push rod 507 is moved towards the joint 501, the amount of snare wire 503 available to form the snare loop 512 is increased, thereby increasing the radius of the snare loop 512. Therefore, in use, a polyp stem or similar tissue can be encircled by the snare loop 512. The operator then retracts the pull rod 507, which closes the snare loop 512 until the tissue is adjacent to the cutting groove 103 in the cap 505. The sharp edges of the cutting groove 103 then act as a reaction surface, enabling the tissue to be cut away from the surrounding bowel wall.

This embodiment is known as a "cold snare" in that no microwave energy is provided to the surgical snare, and it acts by mechanical action alone to remove tissue. Whilst not shown in FIG. 5, it is possible to use the moveable boss as discussed above in such devices. In one embodiment, both ends of the retractable loop can be attached to the movable boss. This arrangement can prevent twisting of the loop during extension and retraction. In another embodiment, one end of the retractable loop is attached to the movable boss and the other is fixed, e.g. in the end cap. The moveable boss can be located behind the joint 501. It is also possible in this embodiment to use a snare wire 503 which is attached at both ends to the push rod 507 i.e. two strands of snare wire 503 attach to the push rod 507, this mechanism can be used in conjunction with the moveable boss described above.

Figure 6A:
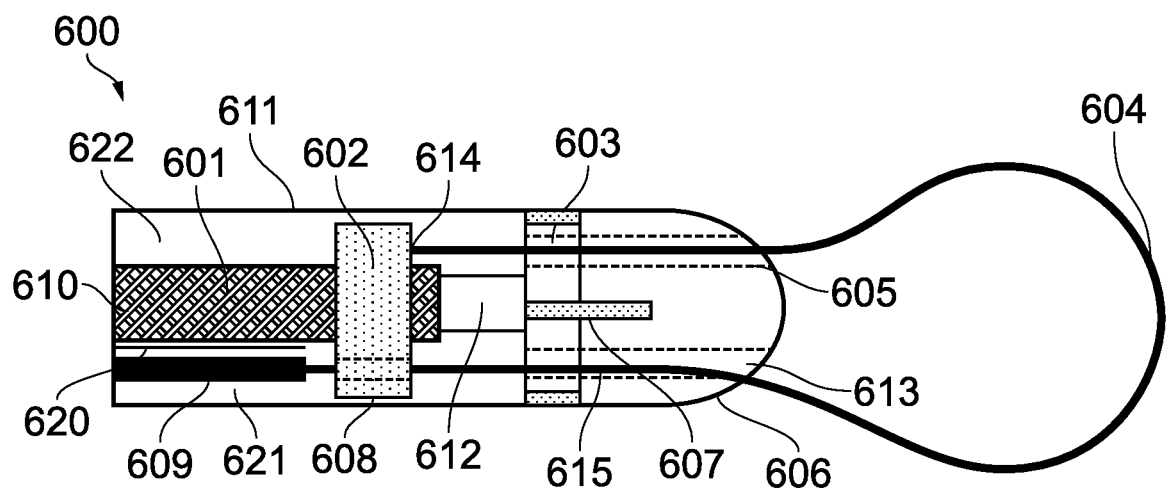
FIG. 6A shows a cross-sectional top-down view of a surgical snare which is another embodiment of the invention.
Figure 6B:
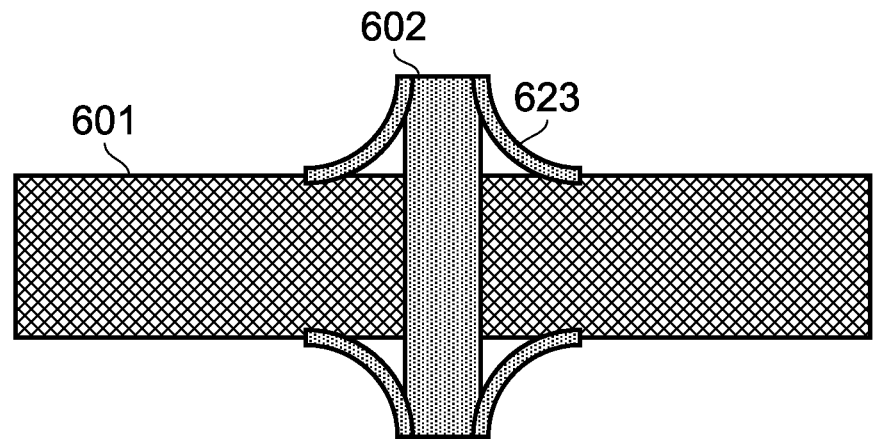
FIG. 6B shows a side-on view of a spring vane connector used in the surgical snare of FIG. 6A.

FIG. 6A shows a top-down cross-sectional surgical snare 600 which is another embodiment of the invention. In this embodiment, the surgical snare 600 comprises an insulating sleeve 611 surrounding a coaxial cable 610. The coaxial cable 610 has an outer conductor 601, an inner conductor 607, and a dielectric 612 separating the inner and outer conductors. The outer conductor 601 terminates after passing through an earth ring 602, and before a joint 603. The dielectric 612 and inner conductor 607 extend beyond the termination of the outer conductor 601, terminating adjacent to a joint 603. The inner conductor 607 then extends into a distal end cap 606. The end cap 606 in this embodiment is that shown in FIGS. 1A and 1B, such that the inner conductor 607 extends into the inner conductor recess 106 of the cap 606. The inner conductor 607 is therefore electrically connected to the conductive tip 107 of the cap 606. FIG. 6B shows a spring vane connection between the outer conductor 601 and earth ring 602. Here the earth ring 602 is connected via spring vanes 623 to the outer conductor 601. These spring vanes 623 are preferably made of an electrically conductive material, to aid in ensuring a good electrical contact between the earth ring 602 and outer conductor 601.

The earth ring 602 is connected (e.g. by soldering, crimping, or welding) to the outer conductor 601, as well as to a first end 614 of a snare wire 615 to fix this portion 614 of the snare wire 615 in place. As discussed above, spring vanes or the like may be used to ensure good electrical contact is made. Therefore the snare wire 615 is electrically connected to the outer conductor 601 of the coaxial cable 610. A push rod 609 is again present, and again extends from the operator end of the endoscope to the surgical snare 500 through the instrument channel of the endoscope. The push rod 609 connects directly to a second end of the snare wire 615. A portion 608 of the snare wire 615 extends through the earth ring 602 to the push rod 609. In contrast to the first end 614 of the snare wire 615, this portion 608 is free to move within the earth ring 602. The snare wire 615 then extends through a first channel 613 of the cap 606. The snare wire 615 then extends freely from the cap 606 so as to form a snare loop 604 by extending through a second channel 605 of the cap 606.

Therefore, in use, the push rod 609 can be moved forwards or backwards as discussed with relation to FIG. 5 to increase or decrease the radius of the snare loop 604. In contrast to the embodiment of FIG. 5 however, the surgical snare 600 may also utilize microwave energy in addition to mechanical action. Microwave energy may be provided via the coaxial cable 610 such that the inner conductor 607 and conductive tip 107 of the cap 606 may radiate microwave energy into biological tissue. The conductive tip 107 preferably functions as a monopole antenna so as to radiate the microwave energy supplied by the coaxial cable 610.

The insulating sleeve 611 may be a multi-lumen tube arranged to convey the push rod 609 or snare wire in a first longitudinal passageway 621 which is separated from a second longitudinal passageway 622 for conveying the coaxial cable 610 by a suitable partition 620.

Figure 7:
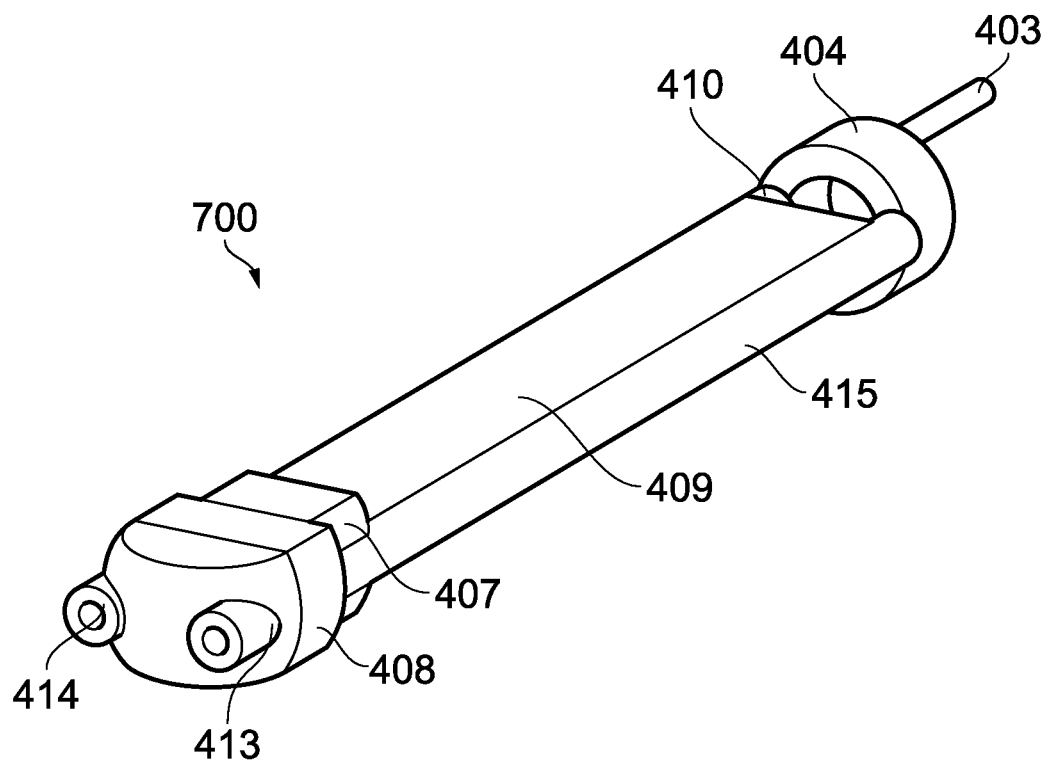
FIG. 7 shows a perspective view of a model of the surgical snare of FIG. 4 used to simulate the microwave delivery performance of the invention.

FIG. 7 depicts a representative model 700 of a surgical snare as shown in FIG. 4 with the snare loop, coaxial cable, and insulation sleeve omitted for clarity. It was modelled using CST MICROWAVE STUDIO®, and the performance simulated as various modifications were made to the structure to improve the return loss (impedance match into tissue load model) and power density in the tissue. Where appropriate reference numerals indicate the corresponding features from FIG. 4.

Figure 8:
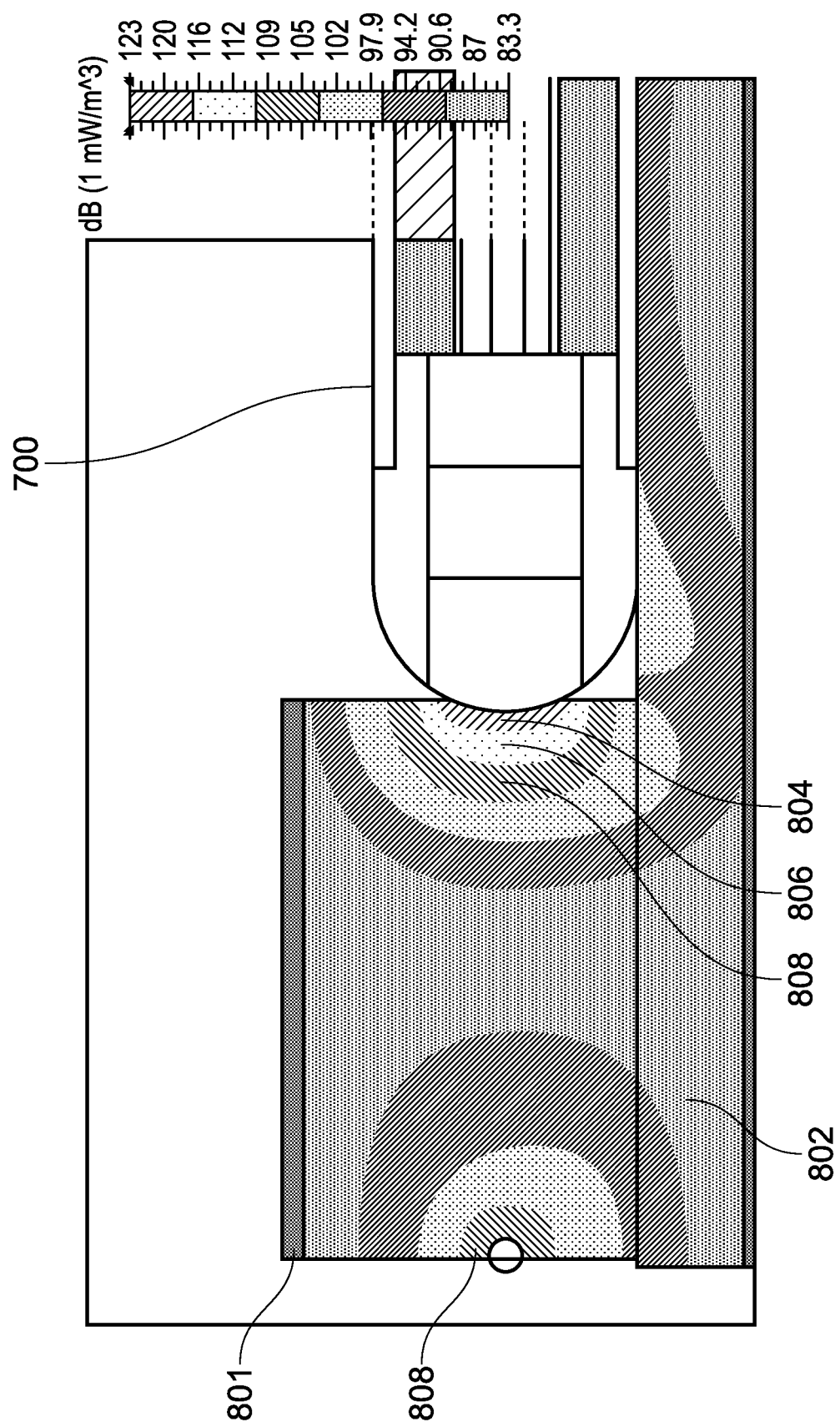
FIG. 8 shows a side view of simulated power loss density into a polyp stem from the model surgical snare shown in FIG. 7.

FIG. 8 is a cross-sectional side-view of the model surgical snare 700 shown in FIG. 7 (with an snare loop in place beyond the distal end thereof) showing power loss density into a polyp stem 801. The polyp stem 801 was modelled as a cylinder with a diameter of 5 mm, and height of 2 mm from a tissue base which is 1 mm in thickness. The snare loop is approximately 4 mm wide and 5 mm long. The cross-section has been taken along the middle of the surgical snare 700. The snare loop is wrapped around and cuts into the polyp stem 801. The polyp stem 801 is connected to the gut wall 802, and both were modelled as liver tissue i.e. with a high blood content. The dielectric properties of liver used in the simulation were as follows:

| | Conductivity [S/m] | Relative permittivity | Loss tangent | Wavelength [m] | Penetration Depth [m] |
|---|---|---|---|---|---|
| Liver | 4.6417 | 38.13 | 0.37727 | 0.0082302 | 0.0071829 |

The average specific heat capacity of blood is 3617 J/kg·° C. (range 3300 J/kg·° C. to 3900 J/kg·° C.) and the average density of blood is 1050 Kg/m$^3$ (range 1025 Kg/m$^3$ to 1060 Kg/m$^3$). Therefore, the average specific heat capacity of blood is around 3.6 J/(g·K), and that the density of tissue is about 1050 Kg/m$^3$=1.05 g/cm$^3$, so that the volumetric heat capacity of the tissue is about 3.6 J/(g·K)×1.05 g/cm$^3$=3.78 J/(K·cm$^3$).

The polyp stem 801 within the snare loop has a power absorption ranging from around 83.3-123 dBm/m$^3$ (0.213-1995 W/cm$^3$) for the modelled 1 W input power. In FIG. 8 the region 804 closest to the end cap indicates a power absorption of 112 dBm/m$^3$ to 118 dBm/m$^3$ (158-630 W/cm$^3$, which corresponds to a temperature increase of 41.8 K/s to 167 K/s. Region 806 represents a power absorption of around a tenth of the region 804, and so indicates a temperature increase of 4.2 K/s to 16.7 K/s. Regions 808, present both at the end cap and at a distal portion of the loop, represent a power absorption of around third of the region 806, and therefore indicate a temperature increase of 1.4 K/s to 5.6 K/s.

Figure 9:
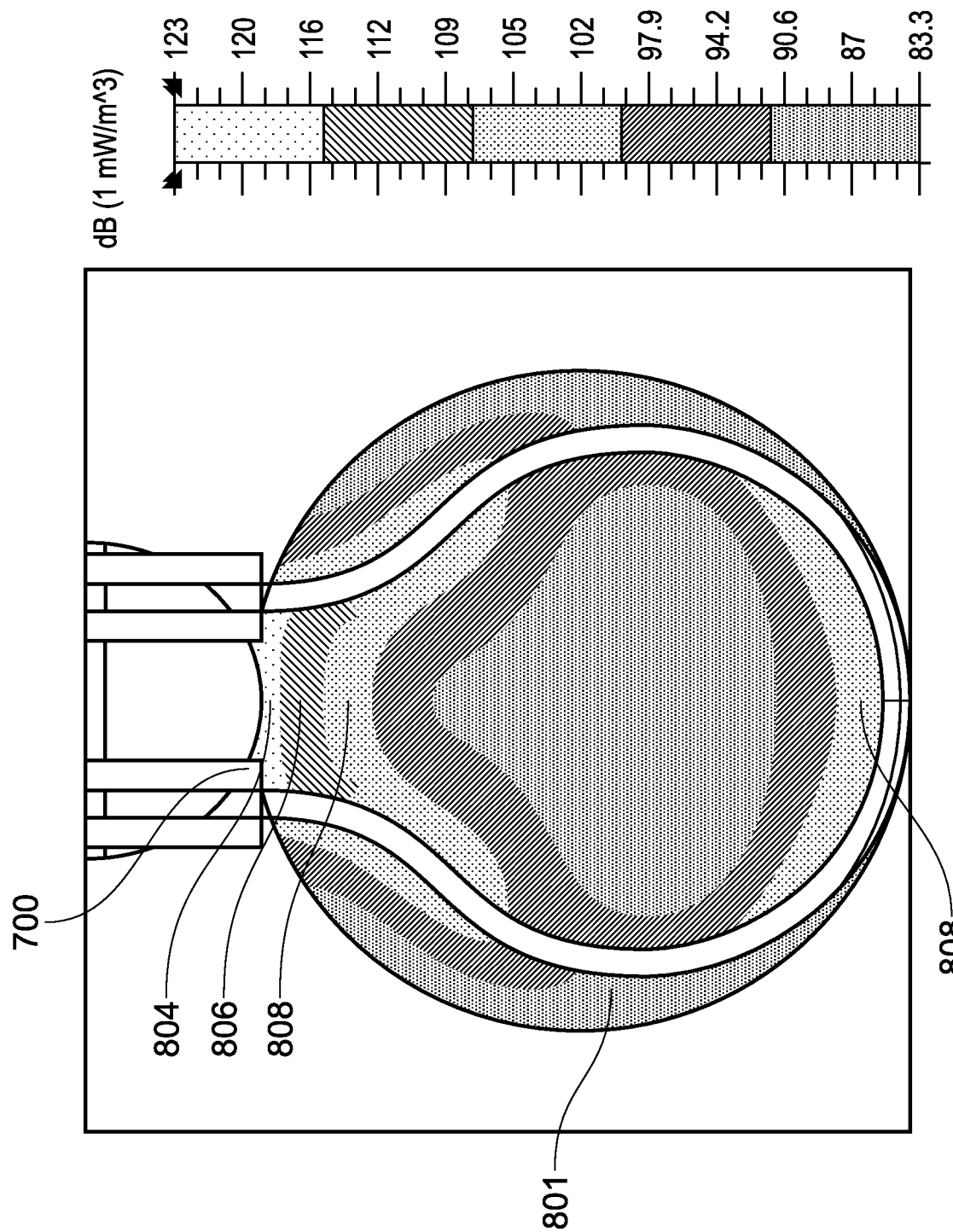
FIG. 9 shows a top view of simulated power loss density into a polyp stem from the model surgical snare shown in FIG. 7.

FIG. 9 is a top-down cross-sectional view of the scene depicted in FIG. 8 and shows power loss density in the plane of the loop. It can be seen that the delivered power is concentrated both at the reaction surface and on the inside edge of the distal region of the snare loop. This means that energy is supplied from opposing directions as the snare loop closes around the captured tissue. The power loss into the rear of the polyp stalk (i.e. the part furthest from the distal head assembly) is up to 109 dBm/m$^3$, this power loss aids the overall heating of the polyp stalk snared within the loop.

Figure 10:
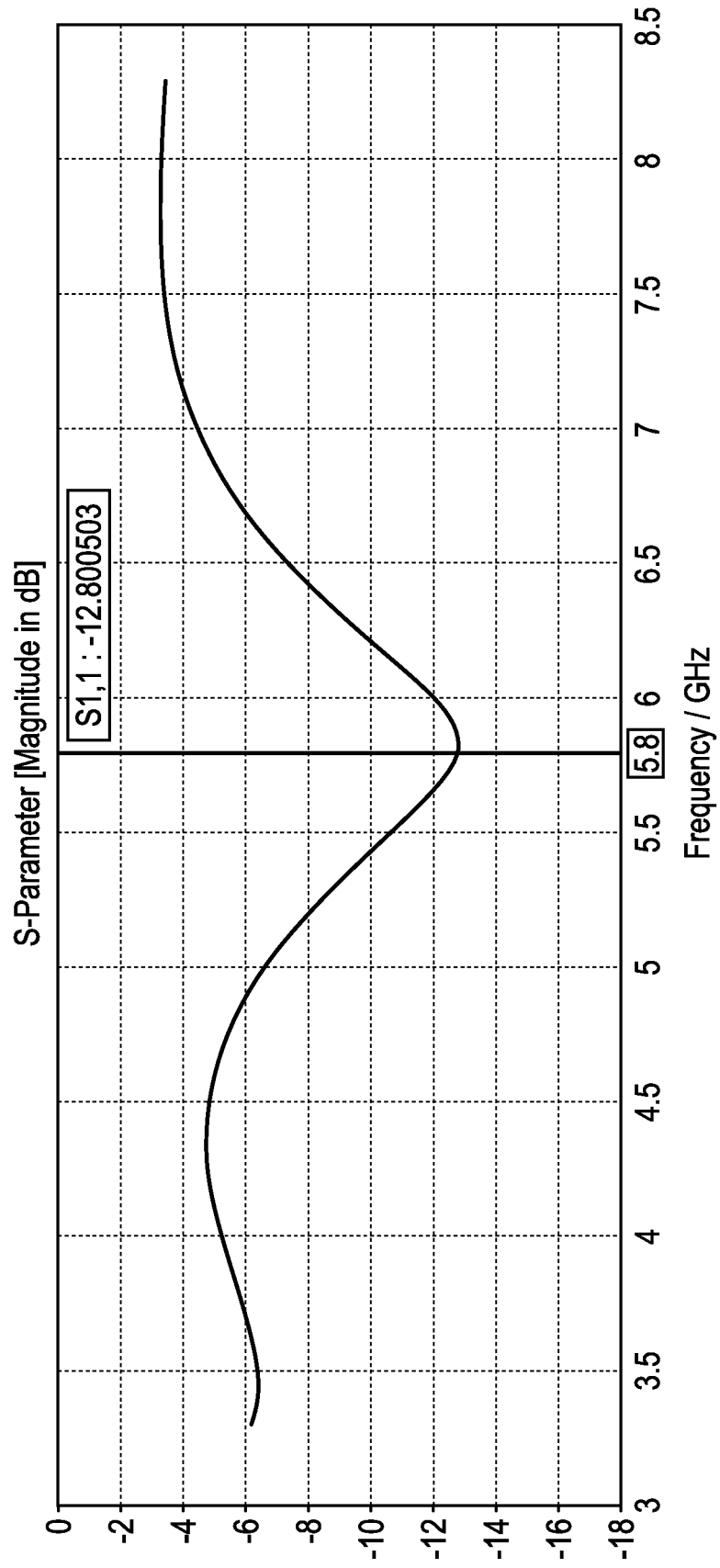
FIG. 10 is a graph showing return loss (impedance match) into liver for the model surgical snare shown in FIG. 7.

FIG. 10 is a graph showing the return loss of the surgical snare 700. The graph represents the $S_{11}$ parameter and therefore the power reflected at the input port. This describes how much of the power is not utilized in the system. As can be seen, there is a dip at 5.8 GHz of around −12.8 dB which indicates that around 5% of the power is reflected. The frequency of the dip can be tuned by adjusting the length of the electrically conductive material in the transformer portion 409. The length for this graph was 12.5 mm.

FIGS. 11A and 11B show a top-down and end-on view respectively of part of a snare 1101, corresponding to the first or second embodiments, in an alternative configuration. In this configuration, the snare loop 1102 is retracted to a near fully retracted position i.e. the snare loop 1102 is very close to the end cap, such that it encircles a very small area in comparison to the other, non-retracted, configuration. FIG. 11A illustrates the electromagnetic field 1103 radiating outward from the snare loop 1102. In this configuration the snare loop 1102 can be energised (i.e. fed electromagnetic energy as discussed above) to coagulate the vessels in the bowel or around the area where the stalk is being removed. In this configuration, it may also be used as a general purpose haemostat to aid coagulation. It may also be used to mark out the region around a sessile tumour before excision, and to stem bleeding in the GI tract and elsewhere.

Figure 12:
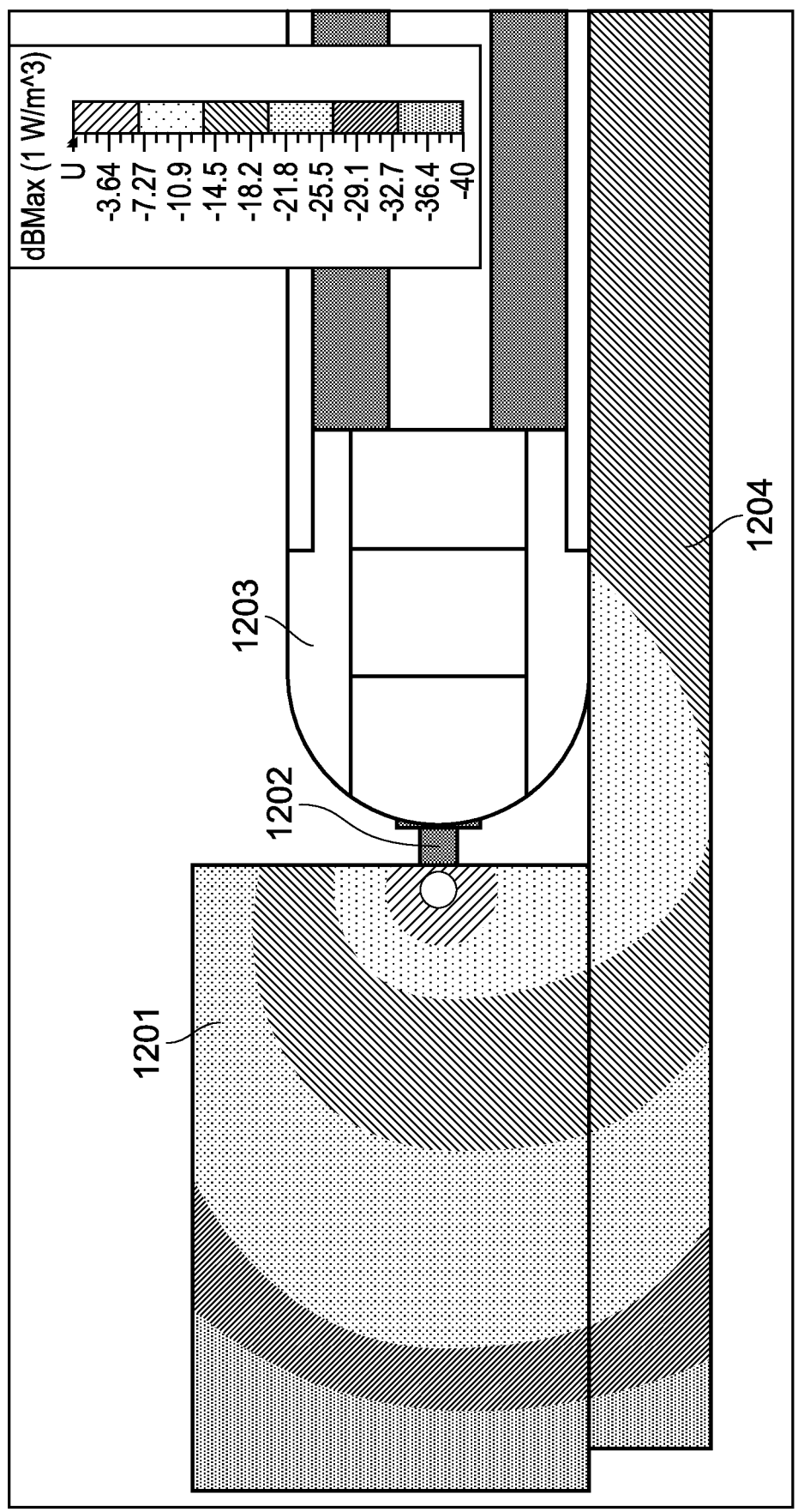
FIG. 12 shows a perspective view of a model of the surgical snare of FIGS. 11A and 11B used to simulate the microwave delivery performance of the invention.

FIG. 12 is a side cross-sectional view of a model snare 1203 in the configuration shown in in FIGS. 11A and 11B and shows power loss density in the plane of the snare loop 1202. The snare loop 1202 intersects a small portion of the simulated polyp 1201, simulating the situation in which the snare loop 1202 is used as a point applicator of microwave energy. It can be seen that the delivered power is concentrated around the snare loop 1202 and radiates outwardly into the polyp stem 1202. In this configuration, there is a slight increase in the power absorbed into the local tissue 1204.

Figure 13:
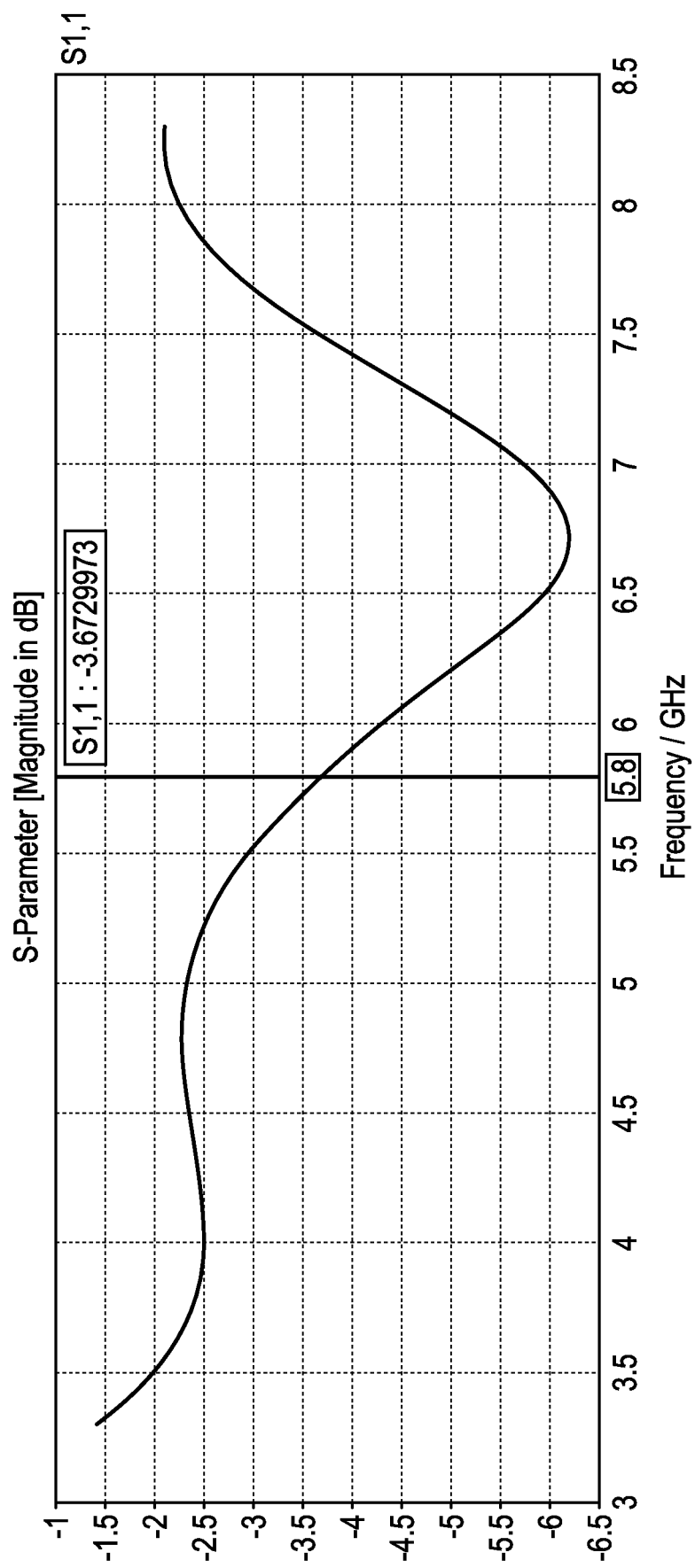
FIG. 13 is a graph showing return loss (impedance match) into liver for the model surgical snare shown in FIGS. 11A and 11B.

FIG. 13 is a graph showing the return loss of the surgical snare into a polyp stem (which is modelled with the dielectric properties of liver). The graph represents the $S_{11}$ parameter and therefore the power reflected at the input port. This describes how much of the power is not utilized in the system. At 5.8 GHz the $S_{11}$ parameter is −3.6 dB, which indicates that around 44% of the power is reflected.

When the loop is fully retracted into the reaction surface (cap), a radiating dome or cylinder will be formed and the device may also be used as a general purpose haemostat.

The invention claimed is:

1. A surgical snare comprising:
   a coaxial cable arranged to convey microwave electromagnetic energy, the coaxial cable having an inner conductor, an outer conductor and a dielectric material separating the inner conductor from the outer conductor;

a distal head assembly disposed at a distal end of the coaxial cable; and a snare wire mounted in the distal head assembly, wherein the distal head assembly comprises an end cap having:
- a distally facing energy transfer structure that is connected to the inner conductor, and
- a pair of channels, each of the pair of channels extending axially between an outlet on the distally facing energy transfer structure and an inlet on a proximal surface of the end cap;

wherein the snare wire is disposed within the pair of channels to form a retractable loop beyond the distally facing energy transfer structure, wherein the distal head assembly includes a fixed boss mounted on the coaxial cable and electrically connected to the outer conductor, wherein the snare wire is electrically connected to the fixed boss, and wherein the distally facing energy transfer structure is configured as an antenna to radiate microwave electromagnetic energy received from the coaxial cable.

2. A surgical snare according to claim 1, wherein the antenna is formed from an electrically conductive material or a low-loss dielectric that enables an effective propagation of microwave energy.

3. A surgical snare according to claim 2, wherein the low-loss dielectric is a ceramic.

4. A surgical snare according to claim 1, wherein the coaxial cable is arranged to convey radiofrequency (RF) electromagnetic energy, and wherein the distally facing energy transfer structure comprises an electrically conductive material electrically connected to the inner conductor.

5. A surgical snare according to claim 4, wherein the distally facing energy transfer structure comprises an electrically conductive surface formed on the end cap.

6. A surgical snare according to claim 1, wherein the snare wire comprises an electrically conductive material electrically connected to the outer conductor.

7. A surgical snare according to claim 6, wherein the snare wire is electrically insulated from the inner conductor and the distally facing energy transfer structure.

8. A surgical snare according to claim 7, wherein the end cap comprises an electrically conductive body electrically connected to the inner conductor, wherein the pair of channels are holes through the electrically conductive body, and wherein the holes have an insulating layer on their inner surfaces to electrically insulate the snare wire from the electrically conductive body.

9. A surgical snare according to claim 1, wherein the snare wire is slidably mounted in the distal head assembly, whereby the loop is retractable towards the distally facing energy transfer structure.

10. A surgical snare according to claim 9, wherein the distally facing energy transfer structure provides a reaction surface for contacting the retractable loop when fully retracted.

11. A surgical snare according to claim 10, wherein the distally facing energy transfer structure includes a distally facing conductive surface, and wherein the reaction surface is a strip of insulating material across the distally facing conductive surface.

12. A surgical snare according to claim 10, wherein the reaction surface is a groove in the reaction surface.

13. A surgical snare according to claim 10, wherein the reaction surface includes a sharpened edge to facilitate cutting of biological tissue captured by the snare wire.

14. A surgical snare according to claim 1, wherein the distally facing energy transfer structure is rounded.

15. A surgical snare according to claim 14, wherein the distally facing energy transfer structure is a dome, wherein the outlets of the pair of channels are located on the dome.

16. A surgical snare according to claim 1, wherein the end cap has insulating cover portions on its side surfaces that are aligned with a plane of the retractable loop.

17. A surgical snare according to claim 1, wherein a first end of the snare wire is attached to a push rod that is axially slidable relative to the coaxial cable, and a second end of the snare wire is attached to the fixed boss.

18. A surgical snare according to claim 17, wherein the push rod comprises a movable boss that is slidably mounted on the coaxial cable.

19. A surgical snare according to claim 1, wherein a first end and a second end of the snare wire are attached to a push rod which is axially slidable relative to the coaxial cable, and the snare wire passes through the fixed boss.

20. A surgical snare according to claim 1, wherein a first end and a second end of the snare wire are joined to form a common snare wire, the common snare wire being attached to a push rod which is axially slidable relative to the coaxial cable.

21. A surgical snare according to claim 1,
wherein the distal head assembly includes an impedance transformer portion mounted between a distal end of the coaxial cable and the end cap, the impedance transformer portion being arranged to match an impedance of the coaxial cable to an impedance of the end cap and tissue to be treated.

22. A surgical snare according to claim 21, wherein the impedance transformer portion includes:
- a length of electrically conductive material extending axially between a distal end of the inner conductor and a proximal surface of the end cap; and
- a pair of passages that extend axially on opposing sides of the length of electrically conductive material,
wherein the snare wire passes through the pair of passages.

23. A surgical snare according to claim 22, wherein the passages are lined with an insulator thereby isolating the snare wire from the inner conductor.

24. A surgical snare according to claim 1, having a sleeve arranged to enclose side surfaces of the distal head assembly.

25. A surgical snare according to claim 24, wherein the sleeve is slidable relative to the distal head assembly to enclose the retractable loop.

26. A surgical snare according to claim 24, wherein the coaxial cable is contained within the sleeve.

27. A surgical snare according to claim 26, wherein the sleeve has an internal longitudinal partition which separates an internal volume of the sleeve into a first longitudinal cavity for carrying the coaxial cable and a second longitudinal cavity for carrying a push rod that is connected to the snare wire.

28. A surgical snare according to claim 1, wherein the end cap has an insulating or non-stick coating.

29. A surgical snare comprising:
- a coaxial cable having an inner conductor, an outer conductor and a dielectric material separating the inner conductor from the outer conductor;
- a distal head assembly disposed at a distal end of the coaxial cable, the distal head assembly having an end cap that is electrically connected to the inner conductor; and a snare wire slidably mounted in the distal head assembly to form a retractable loop beyond the end cap,
wherein a first end of the snare wire is connected to a movable boss that is slidably mounted on the coaxial cable.

30. A surgical snare according to claim 29, wherein the snare wire is electrically connected to the outer conductor and electrically insulated from the inner conductor.

31. A surgical snare according to claim 29, wherein the distal head assembly includes a fixed boss mounted on the coaxial cable, and wherein a first end of the snare wire passes through the fixed boss.

32. A surgical snare according to claim 31, wherein a second end of the snare wire is attached to the fixed boss.

33. A surgical snare according to claim 31, wherein a second end of the snare wire joins the first end of the snare wire between the fixed boss and a moveable boss.

34. A surgical snare according to claim 33, wherein the second end of the snare wire passes through the fixed boss.

35. A surgical snare according to claim 31, wherein the fixed boss is electrically connected to the outer conductor.

36. A surgical snare according to claim 29, wherein a second end of the snare wire is attached to the movable boss.

37. A surgical snare according to claim 29, wherein the movable boss is attached to a push rod that is axially slidable relative to the coaxial cable.

* * * * *